(12) United States Patent
Igaue

(10) Patent No.: US 10,195,074 B2
(45) Date of Patent: Feb. 5, 2019

(54) DISPOSABLE BODY WARMER

(71) Applicant: KOBAYASHI PHARMACEUTICAL CO., LTD., Osaka-shi (JP)

(72) Inventor: Tsuyoshi Igaue, Ibaraki (JP)

(73) Assignee: KOBAYASHI PHARMACEUTICAL CO., LTD., Osaka-shi (JP)

( * ) Notice: Subject to any disclaimer, the term of this patent is extended or adjusted under 35 U.S.C. 154(b) by 518 days.

(21) Appl. No.: 15/026,081

(22) PCT Filed: Oct. 30, 2013

(86) PCT No.: PCT/JP2013/079367
§ 371 (c)(1),
(2) Date: Mar. 30, 2016

(87) PCT Pub. No.: WO2015/045188
PCT Pub. Date: Apr. 2, 2015

(65) Prior Publication Data
US 2016/0242960 A1  Aug. 25, 2016

(30) Foreign Application Priority Data

Sep. 30, 2013 (WO) ............... PCT/JP2013/076626

(51) Int. Cl.
*A61F 7/03* (2006.01)
(52) U.S. Cl.
CPC ................... *A61F 7/034* (2013.01)
(58) Field of Classification Search
CPC combination set(s) only.
See application file for complete search history.

(56) References Cited

U.S. PATENT DOCUMENTS 5,366,492 A * 11/1994 Ueki ............... F24V 30/00
607/114
2001/0010847 A1  8/2001 Otsuka et al.
(Continued)

FOREIGN PATENT DOCUMENTS

CN  1798536 A  7/2006
CN  1864653 A  11/2006
(Continued)

OTHER PUBLICATIONS

Machine translation of JP 2009082156 A.*
(Continued)

*Primary Examiner* — Joseph Stoklosa
*Assistant Examiner* — Adam Avigan
(74) *Attorney, Agent, or Firm* — Kratz, Quintos & Hanson, LLP

(57) ABSTRACT

The present invention provides a disposable body warmer that makes it possible to suppress scattering of moisture contained in the exothermic composition from the outer bag, and thereby ensure a desired exothermic duration of the exothermic composition when the disposable body warmer is kept in an unused state for a long period of time. The disposable body warmer is structured such that an exothermic composition that contains moisture and generates heat by contact with air is enclosed in one or more air-permeable inner bags, which are accommodated in an airtight outer bag. The outer bag comprises two accommodation units that are partitioned from each other and capable of containing the one or more inner bags. The one or more inner bags each comprise at least one enclosure unit capable of enclosing the exothermic composition, and are accommodated in each accommodation unit in a manner such that at least one of the enclosure units is overlaid with another enclosure unit. The (Continued)

outer bag is formed by overlaying two wrapping films with each other, sealing an entire outer peripheral edge, and partitioning the accommodation units by sealing. Further, in the disposable body warmer, Parameters A to H are set to satisfy Formula (1) below $$R = A \times B \times \left\{ \frac{1}{2 \times C} - \frac{1}{D} + \frac{1}{E - F \times (G/H)} \right\} \geq 330 \quad \text{Formula (1)}$$

wherein A represents the inclusion amount (g) of the exothermic composition enclosed in each inner bag in each accommodation unit; B represents the moisture content percentage (%) in the exothermic composition; C represents the area (m²) of the accommodation unit; D represents the number of the enclosure units; E represents the length (m) of an outer peripheral sealing of the accommodation unit; F represents the length (m) of an inner peripheral sealing of the accommodation unit; G represents the strength (N/15 mm) of the outer peripheral sealing; and H represents the strength (N/15 mm) of the inner peripheral sealing.

10 Claims, 10 Drawing Sheets

(56) References Cited

U.S. PATENT DOCUMENTS

| | | | | |
|---|---|---|---|---|
| 2006/0135016 A1* | 6/2006 | Iwasaki | ............... | A61F 7/034 442/327 |
| 2006/0154006 A1* | 7/2006 | Usui | ............... | A61F 7/034 428/34.1 |
| 2007/0142882 A1* | 6/2007 | Quincy, III | ............... | A61F 7/034 607/96 |
| 2008/0283037 A1* | 11/2008 | Dodo | ............... | A61F 7/034 126/263.02 |
| 2010/0241199 A1* | 9/2010 | Hidaka | ............... | A61F 7/034 607/96 |
| 2014/0031748 A1* | 1/2014 | Usui | ............... | A61F 7/03 604/113 |

FOREIGN PATENT DOCUMENTS

| | | | | |
|---|---|---|---|---|
| CN | 201356704 Y | | 12/2009 | |
| CN | 102715978 A | | 10/2012 | |
| CN | 202859442 U | | 4/2013 | |
| EP | 1112702 A1 | | 7/2001 | |
| EP | 2044910 A1 | * | 4/2009 | ............ A61F 7/034 |
| JP | S56-155817 | | 11/1981 | |
| JP | S59-26615 | * | 2/1984 | |
| JP | S60-106622 | | 7/1985 | |
| JP | H05-208031 | | 8/1993 | |
| JP | H06-36623 | | 5/1994 | |
| JP | H06-75437 | | 10/1994 | |
| JP | WO 2007080969 A1 | * | 7/2007 | ............ A61F 7/032 |
| JP | 2009082156 A | * | 4/2009 | ............ A61F 7/032 |
| JP | 2013-0944484 A | | 5/2013 | |
| WO | 2007/080969 A1 | | 7/2007 | |
| WO | 2007/081011 A1 | | 7/2007 | |

OTHER PUBLICATIONS

Machine translation of J P S59-26615.*
Chinese Patent Application No. 201380002982.1: First Office Action dated May 11, 2017.
European Patent Application No. 13894897.1: Extended European Search Report dated May 2, 2017.
International Search Report for International Application No. PCT/JP2013/079367 dated Nov. 26, 2013.

* cited by examiner

[FIG. 1]
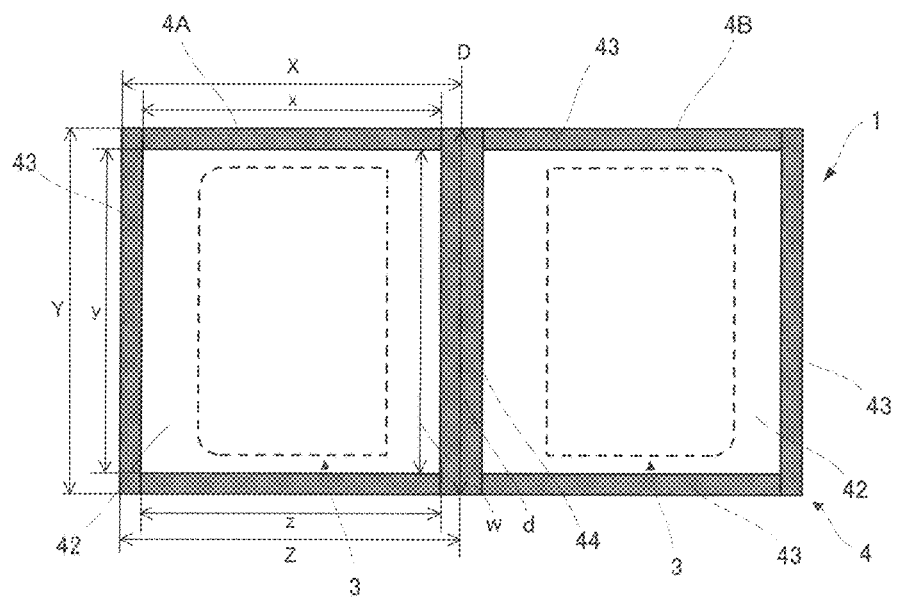
[FIG. 2]
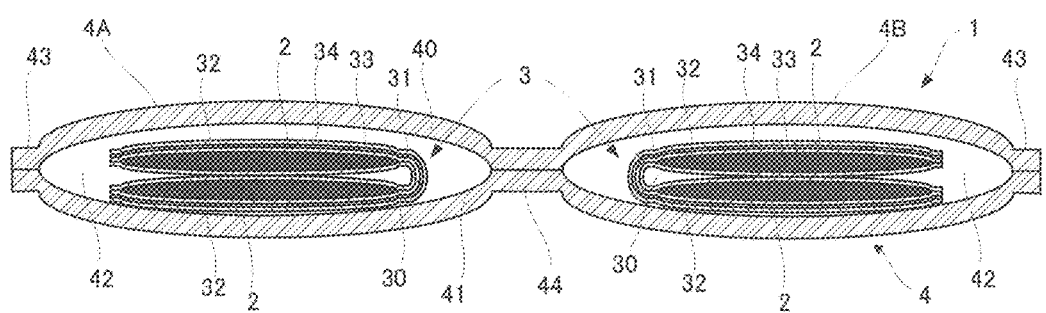

[FIG. 3]
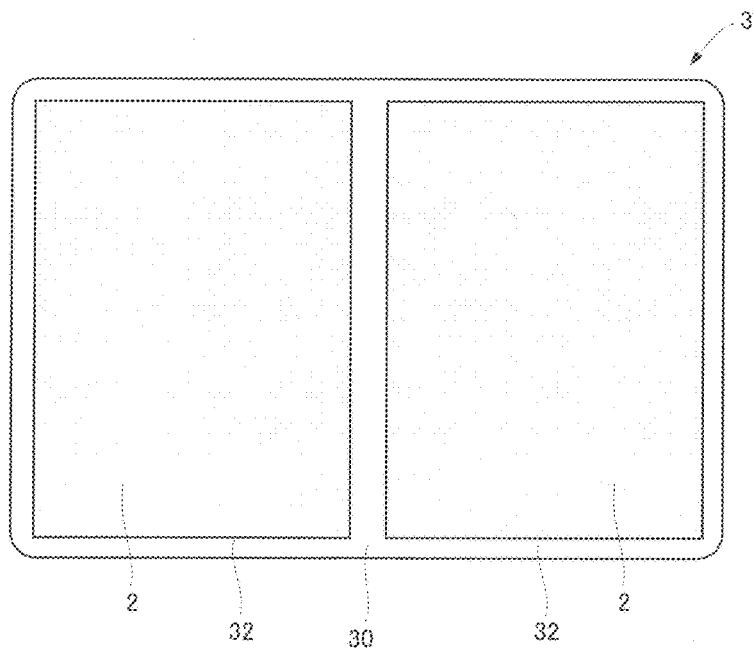
[FIG. 4]
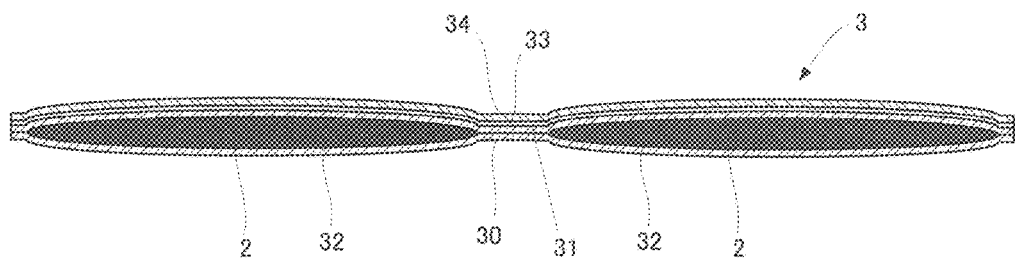

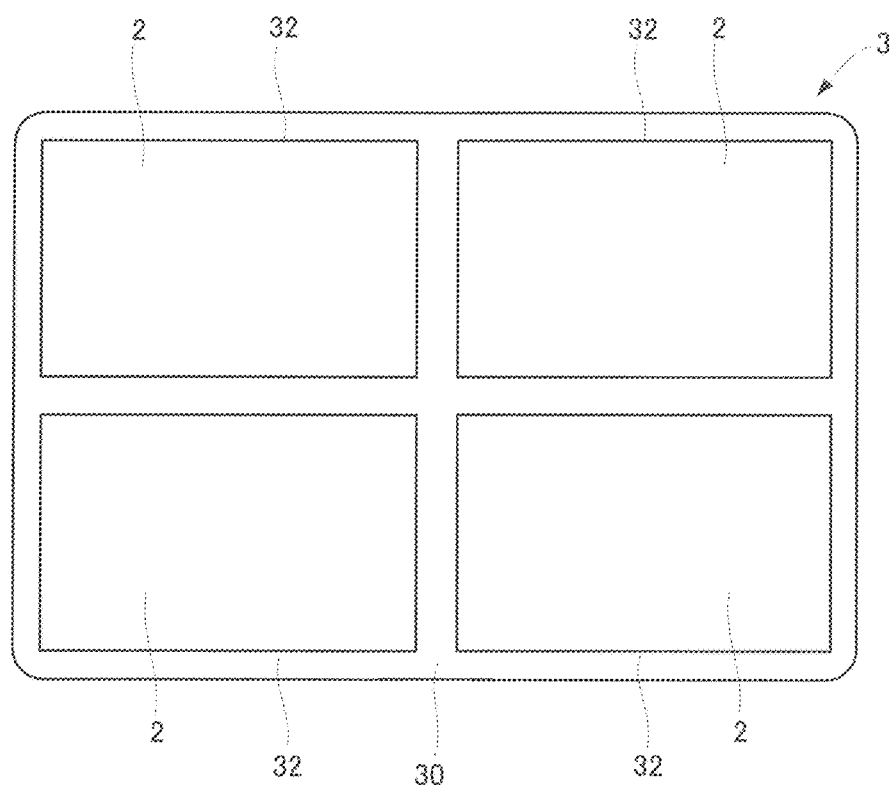
[FIG. 5]

[FIG. 6]
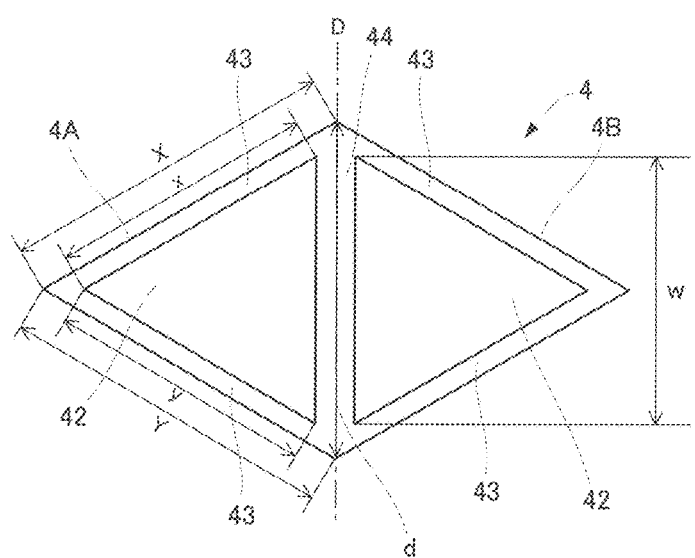
[FIG. 7]
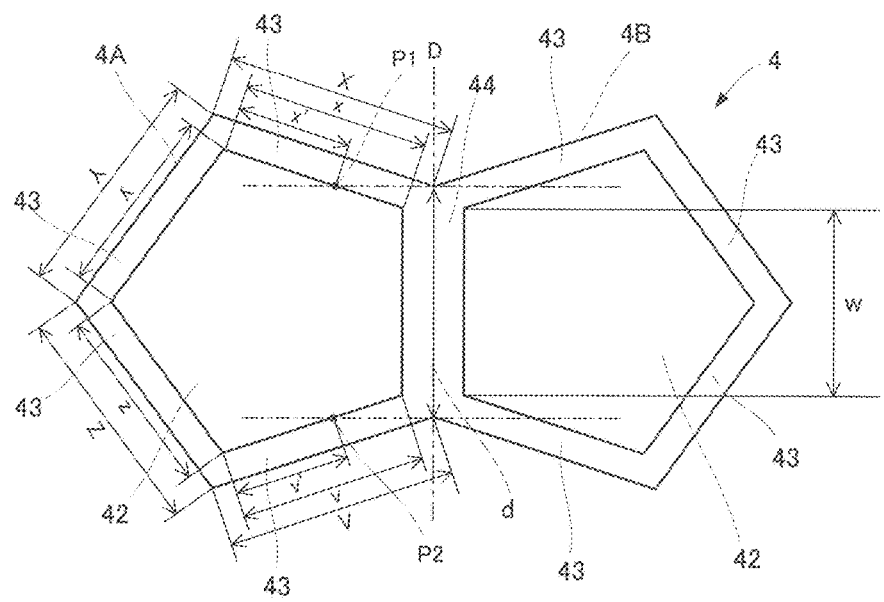

[FIG. 8]
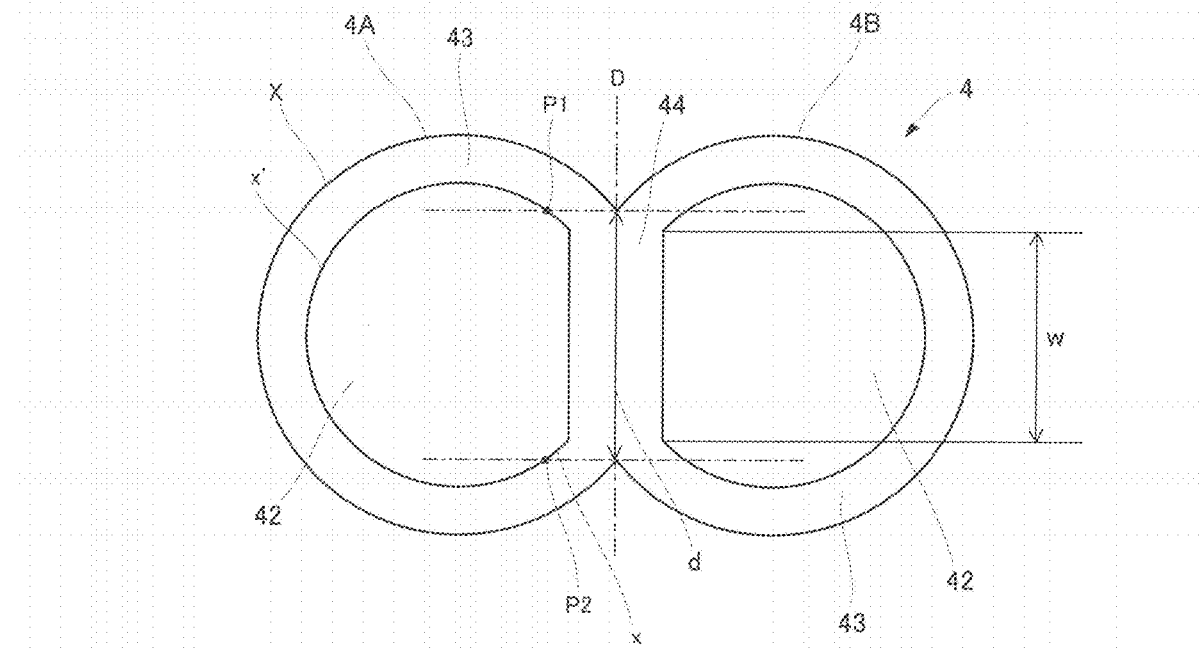
[FIG. 9]
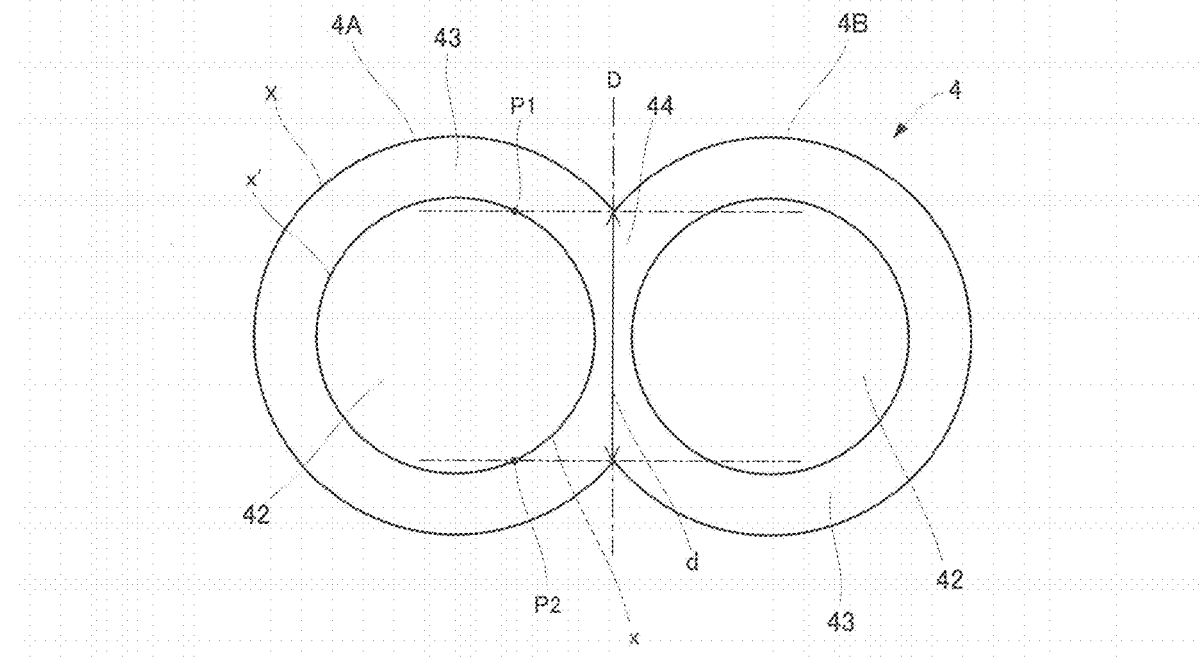

[FIG. 10]
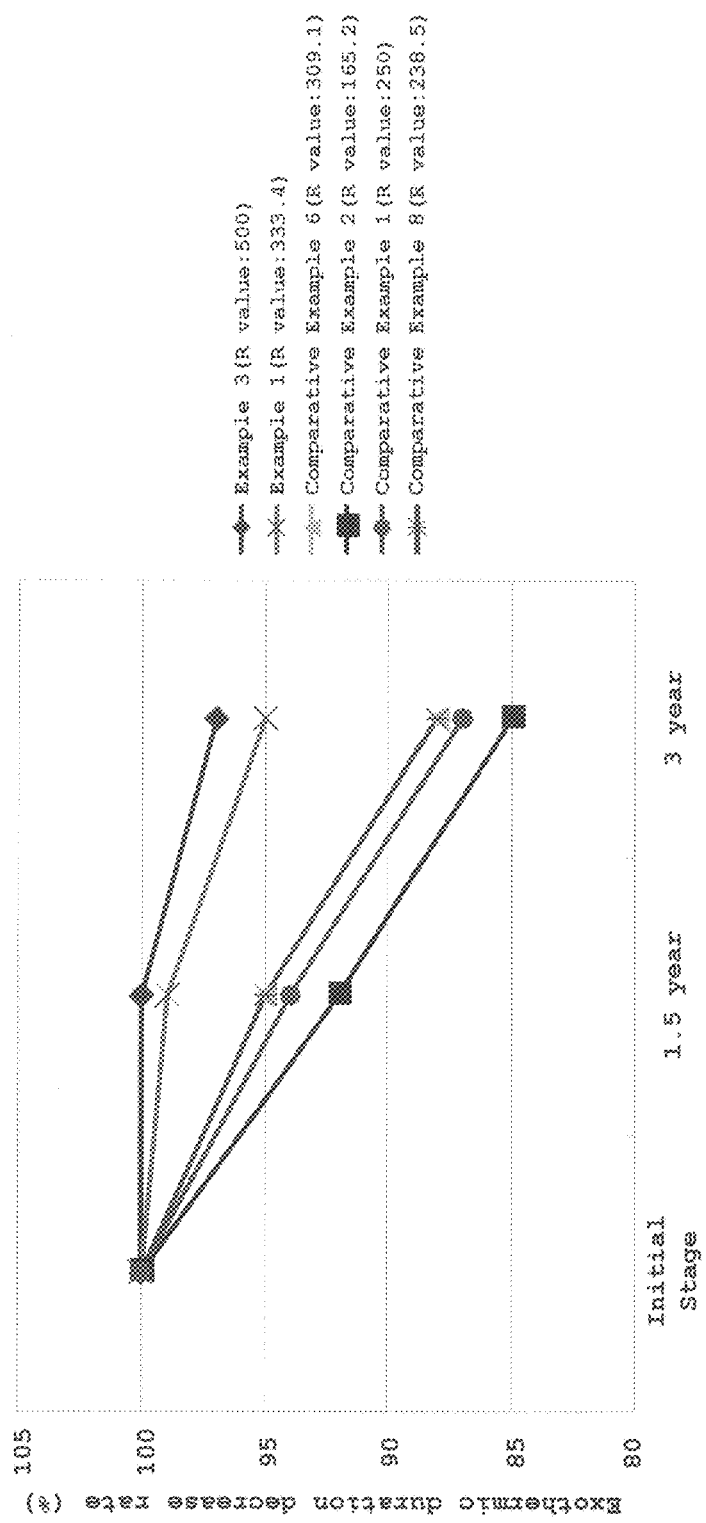

[FIG. 11]
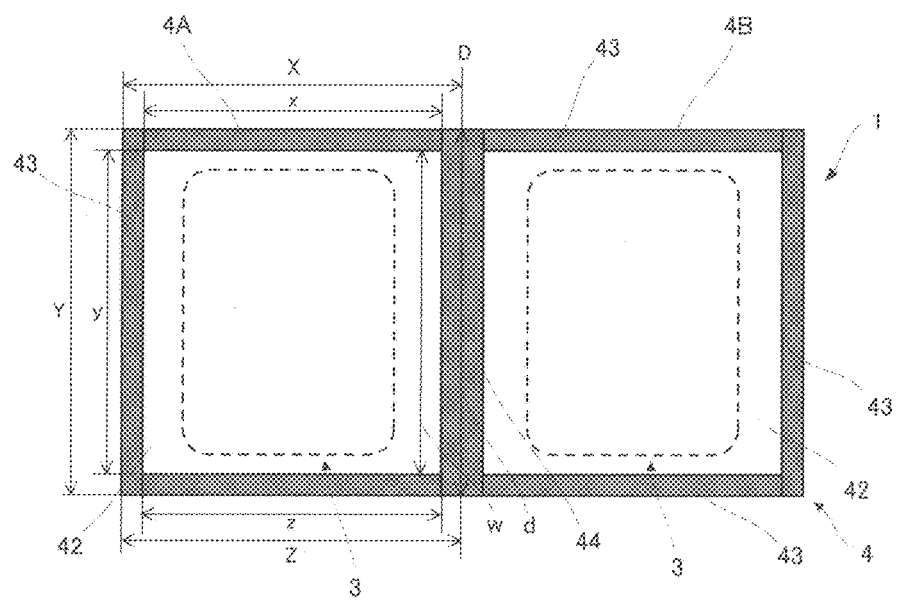
[FIG. 12]
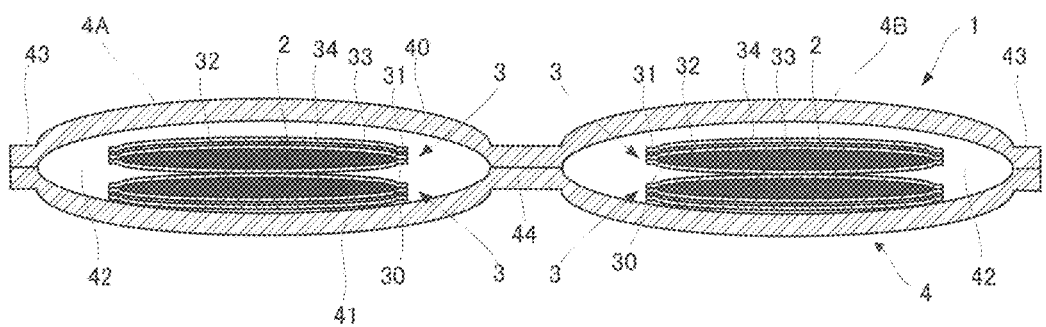

[FIG. 13]
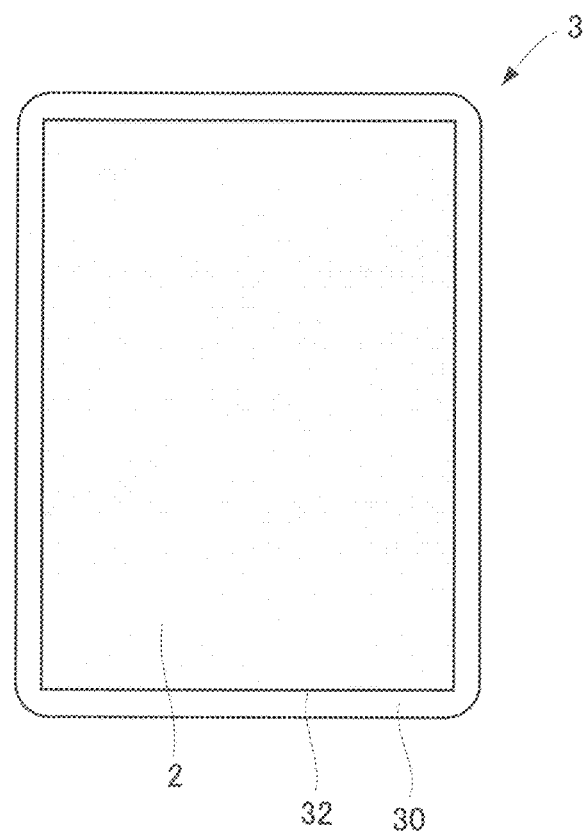
[FIG. 14]
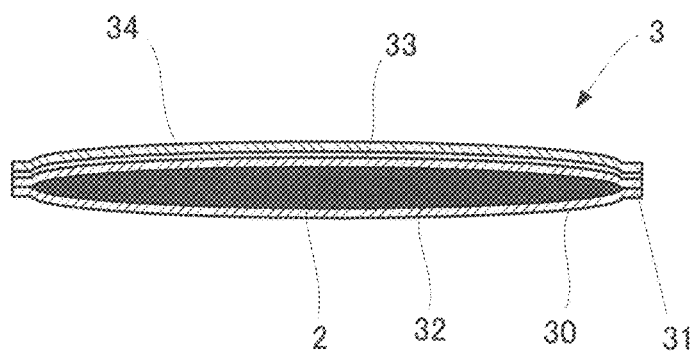

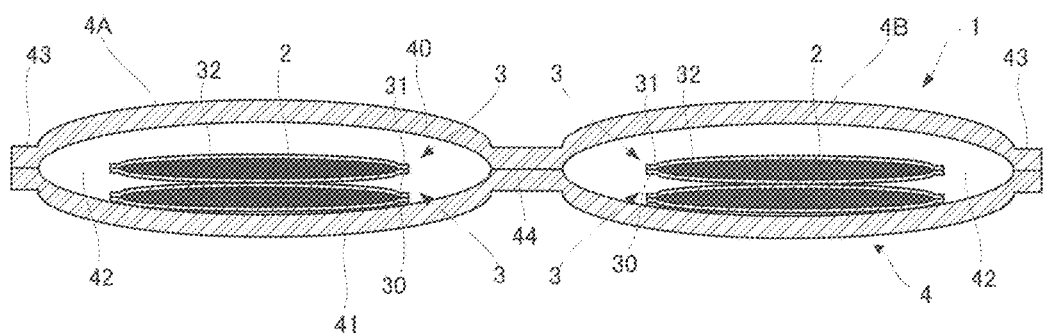
[FIG. 15]

[FIG. 16]
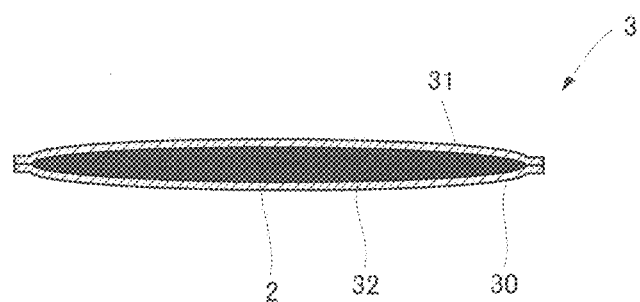
[FIG. 17]
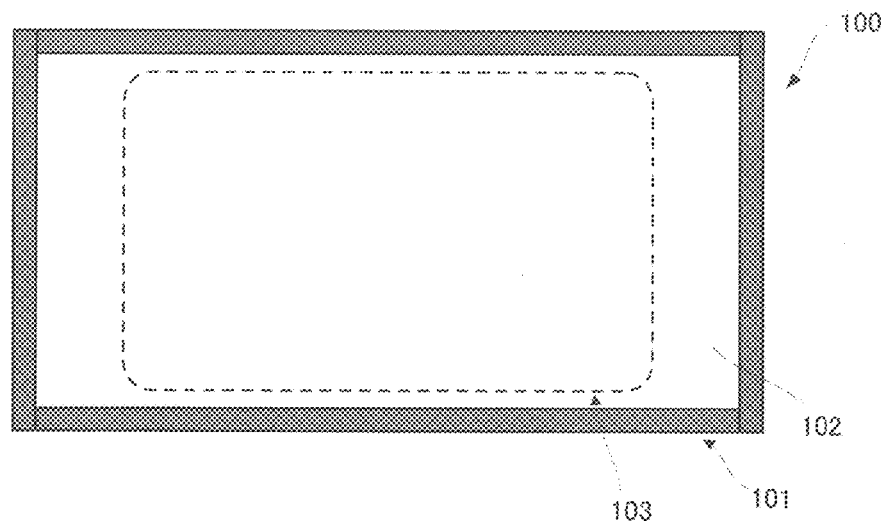

DISPOSABLE BODY WARMER

TECHNICAL FIELD

The present invention relates to a disposable body warmer.

BACKGROUND ART

Conventionally, disposable body warmers enclosing an exothermic composition, which generates heat by contact with air and is enclosed in an air-permeable flat bag (inner bag), have been known as a tool for warming the body. Such disposable body warmers are frequently used because they are excellent in portability, safety, convenience, and the like, and are inexpensive. In an unused state, the inner bag of the disposable body warmer is packaged in an airtight flat bag (outer bag) so as to prevent the exothermic composition from contacting with air. For example, as shown in FIG. 17, a disposable body warmer 100 formed of an outer bag 101 having a single accommodation unit 102, which contains a single inner bag 103, has been generally known.

CITATION LIST

Patent Document

Patent Document: JPH05-208031A

SUMMARY OF INVENTION

Technical Problem

The exothermic conditions (maximum temperature, average temperature, exothermic duration, or the like) of the disposable body warmers are controlled by adjusting the components of the exothermic composition (for example, the content of iron powder serving as an exothermic element, moisture content ratio, or the like) and the like. Water is an essential component of an exothermic composition, and an insufficient moisture content percentage results in a decrease in duration of a disposable body warmer, while an excessive moisture content percentage results in failure of heat generation in a disposable body warmer. Thus, ingenuity is exercised to adjust the moisture content percentage in an exothermic composition. However, research by the present inventors revealed that if a disposable body warmer is kept in an unused state for a long period of time, for example, because the disposable body warmer is kept in a store for a long time, the disposable body warmer in which an inner bag is sealed in an outer bag in a manner shown in FIG. 17 cannot exhibit a sufficient exothermic performance at the time of use, even though the inner bag enclosing the exothermic composition has been sealed in an airtight outer bag; in particular, the exothermic duration period (the duration from the point where the temperature of the heated disposable body warmer exceeds 40° C. to the point where the temperature of the disposable body warmer falls below 40° C.) greatly decreases. Such a decrease in exothermic duration is assumed to occur as the moisture in the exothermic composition is evaporated and scattered from the outer bag during storage. In view of this problem, in conventional body warmers, such a decrease in exothermic duration period has been compensated for by increasing the inclusion amount of the exothermic composition more than necessary, thereby ensuring the desired exothermic duration period after long storage. However, this method poses a drawback of an increase in cost. Therefore, there has been a demand for packaging an inner bag in an outer bag while preventing scattering of moisture as much as possible.

The present invention was made by focusing attention on the above problem, and an object of the present invention is to provide a disposable body warmer that makes it possible to suppress the scattering of moisture contained in the exothermic composition from the outer bag, and thereby ensure a desired exothermic duration of the exothermic composition even when the disposable body warmer is kept in an unused state for a long period of time.

Solution to Problem

The above object of the present invention is accomplished by a disposable body warmer in which an exothermic composition that contains moisture and generates heat by contact with air is enclosed in one or more air-permeable inner bags, which are accommodated in an airtight outer bag, the outer bag comprising two accommodation units that are partitioned from each other and capable of containing the one or more inner bags, the one or more inner bags each comprising at least one enclosure unit capable of enclosing the exothermic composition, and are accommodated in each accommodation unit in a manner such that at least one of the enclosure units is overlaid with another enclosure unit, the outer bag being formed by overlaying two wrapping films with each other, sealing an entire outer peripheral edge, and partitioning the accommodation units by sealing, and Parameters A to H being set to satisfy Formula (1) below, $$R = A \times B \times \left\{ \frac{1}{2 \times C} - \frac{1}{D} + \frac{1}{E - F \times (G/H)} \right\} \geq 330 \quad \text{Formula (1)}$$

wherein A represents the inclusion amount (g) of the exothermic composition enclosed in each inner bag in each accommodation unit; B represents the moisture content percentage (%) in the exothermic composition; C represents the area ($m^2$) of the accommodation unit; D represents the number of the enclosure units, E represents the length (m) of an outer peripheral sealing of the accommodation unit; F represents the length (m) of an inner peripheral sealing of the accommodation unit; G represents the strength (N/15 mm) of the outer peripheral sealing; and H represents the strength (N/15 mm) of the inner peripheral sealing. In this case, the number of the enclosure units is preferably 2 to 4.

In a preferable embodiment of the heating tool having the above structure, each inner bag comprises at least two enclosure units partitioned from each other, and is accommodated in the accommodation unit in a single-folded state so that at least one of the enclosure units is overlaid with another enclosure unit. In this case, the number of the enclosure units is preferably 2 to 4.

In another preferable embodiment of the heating tool having the above structure, each inner bag comprises one enclosure unit, and a plurality of the inner bags are accommodated in each accommodation unit while being stacked on each other so that an enclosure unit of one of the inner bags is overlaid with an enclosure unit of at least one of the other inner bags.

In a further preferable embodiment, one of the enclosure units is disposed lowermost, and all other enclosure units are stacked thereon.

In a further preferable embodiment, an air-impermeable sheet material is stacked on at least one surface of the inner bag, and the enclosure units are stacked in a manner such that the air-impermeable sheet material is positioned as the uppermost surface in the vertical direction.

Advantageous Effects of Invention

Since the disposable body warmer of the present invention makes it possible to suppress the scattering of moisture contained in the exothermic composition from the outer bag, it is possible to ensure a desired exothermic duration of the exothermic composition, even when the disposable body warmer is kept in an unused state for a long period of time.

BRIEF DESCRIPTION OF DRAWINGS

FIG. 1 is a plan view of a disposable body warmer according to one embodiment of the present invention.
FIG. 2 is a cross-sectional view of FIG. 1.
FIG. 3 is a plan view of an inner bag.
FIG. 4 is a cross-sectional view of FIG. 3.
FIG. 5 is a plan view showing a variation of an inner bag.
FIG. 6 is a plan view showing a variation of an outer bag.
FIG. 7 is a plan view showing a variation of an outer bag.
FIG. 8 is a plan view showing a variation of an outer bag.
FIG. 9 is a plan view showing a variation of an outer bag.
FIG. 10 is a graph showing a comparison between the disposable body warmer of the present embodiment and the disposable body warmer of a Comparative Example in terms of an exothermic duration decrease rate.
FIG. 11 is a plan view of a disposable body warmer according to another embodiment of the present invention.
FIG. 12 is a cross-sectional view of FIG. 11.
FIG. 13 is a plan view of the inner bag of FIG. 12.
FIG. 14 is a cross-sectional view of FIG. 13.
FIG. 15 is a cross-sectional view of a disposable body warmer according to another embodiment of the present invention.
FIG. 16 is a cross-sectional view of the inner bag of FIG. 15.
FIG. 17 is a plan view of a conventional disposable body warmer.

DESCRIPTION OF EMBODIMENTS

An embodiment of a disposable body warmer of the present invention is described below with reference to drawings. As shown in FIGS. 1 and 2, a disposable body warmer 1 in this embodiment is structured such that an exothermic composition 2 that generates heat by contact with air is enclosed in an air-permeable flat inner bag 3, and the inner bag 3 is accommodated in an airtight flat outer bag 4. The disposable body warmer 1 provides a thermal effect by taking out the inner bag 3 from the outer bag 4 and applying the exothermic composition 2 in the inner bag 3 on various body parts, including a hand, a foot, a lumbar area, the back, the belly, a sole of foot, a shoulder, a buttock, and the like.

The exothermic composition 2 is made of any material capable of generating heat by contact with air. Examples of the materials include known compositions to be used for disposable body warmers, i.e., the compositions containing, for example, appropriate amounts of oxidizable metal, activated carbon, a water-retaining agent (such as wood flour, vermiculite, diatomaceous earth, perlite, silica gel, alumina, a water-absorbing resin, or the like), metal salts (such as common salts) and water. The oxidizable metal is a metal that generates oxidation reaction heat. Examples of oxidizable metal include powders or fibers selected from one or more kinds of iron, aluminum, zinc, manganese, magnesium, and calcium. Of these, iron powder is preferable in view of easy handling, safety, production cost, preservability, and stability. Examples of iron powder include one or more kinds of reduced iron powder and atomized iron powder. The disposable body warmer 1 is controlled so that it has desired exothermic conditions (maximum temperature, average temperature, exothermic duration, or the like) at the time of use by adjusting the components of the exothermic composition 2. For example, the amount of the oxidizable metal to be incorporated in the exothermic composition 2 is preferably 30% to 80%, more preferably 40% to 70%, further preferably 40% to 65%. Further, water is an essential component of the exothermic composition 2, and since an insufficient moisture content percentage results in a decrease in exothermic duration, ingenuity is exercised to adjust the moisture content percentage in the exothermic composition 2. As is clear from the above, the moisture content percentage in the exothermic composition 2 is an important factor in ensuring desired exothermic duration when the disposable body warmer 1 is used. Therefore, in the disposable body warmer 1 according to this embodiment, ingenuity is exercised in the shapes of the inner bag 3 and the outer bag 4, and the method of containing the inner bag 3 in the outer bag 4, so as to prevent the moisture contained in the exothermic composition 2 from scattering from the outer bag 4 as much as possible even when the disposable body warmer 1 is, for example, kept in a store for a long period of time and thus kept in an unused state for a long time, thereby preventing a decrease in exothermic duration due to a decrease in moisture content percentage in the exothermic composition 2.

As shown in FIGS. 3 and 4, in this embodiment, the inner bag 3 is formed of two rectangular sheet materials, i.e., first and second (front and rear) rectangular sheet materials 30 and 31, and is shaped as a bag having a plurality of (2 in this embodiment) rectangular enclosure units 32, each of which is capable of enclosing the exothermic composition 2, by joining the two sheet materials 30 and 31 with each other and sealing (bonding) the outer peripheral edges (side edges in the four directions) using a known adhesive or by way of thermal bonding (heat-seal). The plurality of enclosure units 32 are partitioned by a sealing of the two sheet materials 30 and 31 at a portion between adjacent enclosure units 32. As shown in FIG. 2, the enclosure units 32 can be overlaid on each other by folding the inner bag 3 at a portion between adjacent enclosure units 32. The number of the enclosure units 32 is not limited to 2, and may be 3 or more, but is preferably 2 to 4. Further, the layout of the plurality of enclosure units 32 is not particularly limited. As shown in FIG. 3, a plurality of enclosure units 32 may be arranged in a row. The enclosure units 32 may also be arranged in multiple vertical columns. For example, when four enclosure units 32 are provided, as shown in FIG. 5, the enclosure units 32 may be arranged in two vertical columns by disposing two enclosure units 32 in each column. In this layout, similarly to the case above, the enclosure units 32 can be overlaid with each other by folding the inner bag 3 at a portion between vertically or horizontally adjacent enclosure units 32.

The first sheet material 30 is air-permeable, and is brought into contact with a user's body at the time of use. The first sheet material 30 may be any air-permeable material, including porous resin films, needle-perforated resin films, non-woven and woven fabrics. Further, the first sheet material 30 may have a single-layer structure, or a multilayer structure formed of a lamination of a resin film and a non-woven fabric. Any resin films having been hitherto used as a material of the inner bag 3 of the disposable body warmer 1 may be used. Examples include polyethylene, polypropylene, polyester, polyamide, polyvinyl alcohol, polyvinyl chloride, polyvinylidene chloride, polyurethane, polystyrene, ethylene-vinyl acetate copolymer, polycarbonate, and hydrochlorinated rubber. Further, examples of non-woven fabric include synthetic fibers such as polypropylene, nylon, vinylon, polyester, polyethylene terephthalate, rayon, acetate, acrylic, polyethylene, or polyvinyl chloride; and natural fibers such as cotton, hemp, or silk. Further, in addition to non-woven fabric, paper and the like may also be used.

The second sheet material 31 may be air-permeable or air-impermeable. As with the first sheet material 30, the second sheet material 31 may be a resin film or a non-woven or woven fabric, and may have a single-layer structure, or a multilayer structure. As shown in FIG. 4, when the second sheet material 31 is air-permeable, an adhesive layer 33 may be provided on the surface. More specifically, by applying, to the surface of the second sheet material 31, an acrylic resin-based or rubber-based resin adhesive agent having an effect of adhering to skin and cloth, it is possible to produce a so-called stick-on-type body warmer. The adhesive layer 33 is covered with a release paper 34 while the inner bag 3 is accommodated in the outer bag 4 until the body warmer is used. In contrast, in the case of a non-stick-type body warmer, which is used, for example, by being held by a hand, an air-permeable sheet is used as the second sheet material 31, and the adhesive layer 33 and the release paper 34 are not provided. However, at least one surface of the first sheet material 30 and the second sheet material 31 may be covered with an air-impermeable sheet material while the inner bag 3 is accommodated in the outer bag 4 until the body warmer is used.

In this embodiment, the inner bag 3 is structured such that the two partitioned enclosure units 32 are integrally formed by sealing the two sheet materials 30 and 31 at the outer peripheral edges (side edges in the four directions) and at the center. However, for example, it is also possible to individually produce two compact-sized inner bags, each of which has an enclosure unit 32, and then join them together by bonding the binding margins in the peripheral edges of the two inner bags.

In each enclosure unit 32, the proportion of the capacity of the enclosed exothermic composition 2 with respect to the capacity of the enclosure unit is preferably about 30% to 80%, particularly preferably about 50% to 70%. When the proportion is more than 80%, the content of the exothermic composition 2 becomes excessive, and thus the exothermic composition 2 enters into the sealing portion when the inner bag 3 having a plurality of enclosure units 32 is formed by sealing the two sheet materials 30 and 31. This may result in failure of the formation of the inner bag 3. On the other hand, if the proportion is less than 30%, the desired exothermic conditions may not be satisfied at the time of use of the disposable body warmer 1. Further, the area of the enclosure unit 32 is preferably not more than 0.05 m$^2$. If the area of the enclosure unit 32 is more than 0.05 m$^2$, the area of the accommodation unit 42 (described later) of the outer bag 4 for containing the inner bag 3 increases, thereby increasing the entire size of the outer bag 4. This may result in drawbacks such as an increase in bulkiness of the portable body warmer, an increase in cost due to an increase in the amount of the outer bag 4 (wrapping films 40 and 41), and the like.

As shown in FIGS. 1 and 2, the outer bag 4 is formed of two (front and rear) rectangular wrapping films 40 and 41, and is formed as a bag having two rectangular accommodation units 42, each of which is capable of containing the inner bag 3; and first sealing portions 43 for sealing the outer bag 4 on the outer peripheral edges (side edges in the four directions). This outer bag 4 is produced by joining the two wrapping films 40 and 41 with each other, and sealing (bonding) the outer peripheral edges (side edges in the four directions) by, for example, thermal bonding (heat-seal) or using a known adhesive. Between the two accommodation units 42, the second sealing portion 44 is formed by linearly sealing (bonding) the two wrapping films 40 and 41 so that the two accommodation units 42 are partitioned by the second sealing portion 44.

Any films having been used as materials of the outer bag 4 of the disposable body warmer 1 may be used as the wrapping films 40 and 41. Examples include polyethylene, polypropylene, silica deposition film, vinylidene chloride-coated film, and like nonporous films. Of these, in terms of oxygen or vapor impermeability and appropriate hydrogen permeability, vinylidene chloride-coated films (KOP, K-nylon, KPET, etc.) and aluminum deposition-coated films (VMPET, VMCPP, etc.) are preferable.

The disposable body warmer 1 in this embodiment is characterized in that the inner bags 3 are accommodated in individual accommodation units 42 of the outer bag 4 in a manner such that each inner bag 3 is folded at least once so that at least one enclosure unit 32 of the inner bag 3 is overlaid with another enclosure unit 32. More specifically, for example, when two enclosure units 32 are provided in each inner bag 3, as shown in FIG. 2, one of the enclosure units 32 is overlaid with another enclosure unit 32 by folding the inner bag 3 at its center. The inner bag 3 in such a state is accommodated in individual accommodation units 42 of the outer bag 4. By thus overlaying the enclosure units 32 on one another, the area (the total surface area for containing the multiple enclosure units 32) of the inner bag 3 may be reduced by half, thereby reducing the area subjected to external contact of the exothermic composition 2 enclosed in the enclosure unit 32. As a result, it is possible to prevent easy scattering of the moisture in the exothermic composition 2 enclosed in each enclosure unit 32. Further, by containing the inner bags 3 in a folded state in the outer bag 4, the area of the accommodation unit 42 of the outer bag 4 for containing the inner bags 3 may be reduced, compared with the case of containing the inner bags 3 in an unfolded state. By thus reducing the area, it is possible to also reduce passing of the moisture in the exothermic composition 2 through the front and rear surfaces (the wrapping films 40 and 41) of the accommodation unit 42, and thereby reduce scattering of the moisture to the outside of the accommodation unit 42. Moreover, by containing the inner bags 3 in a folded state, the required amount of the outer bag 4 (the wrapping films 40 and 41) may be reduced, compared with the case of containing the inner bags 3 in an unfolded state, thereby reducing the cost.

In this case, each inner bag 3 is preferably folded so that when the second sheet material 31 is air-impermeable, the second sheet material 31 is positioned as the uppermost surface in the vertical direction; and when the second sheet material 31 is air-permeable, the air-impermeable sheet material (not shown) that covers at least one of the first sheet material 31 and the second sheet material 32 is positioned as the uppermost surface in the vertical direction. With this structure, the uppermost surface in the vertical direction of the lamination of the enclosure units 32 becomes air-impermeable, thereby more effectively preventing easy scattering of the moisture in the exothermic composition 2 enclosed in each enclosure unit 32.

Further, in the case where three enclosure units 32 are provided in each inner bag 3, the inner bags 3 may be accommodated in individual accommodation units 42 of the outer bag 4 while being folded once between an enclosure unit 32 at one end and the enclosure unit 32 at the center, that is, only two of the enclosure units 32 are overlaid with each other. However, more preferably, the inner bags 3 are accommodated in individual accommodation units 42 of the outer bag 4 while being folded twice, i.e., also at an enclosure unit 32 at the other end, that is, all three enclosure units 32 are overlaid on one another. With this structure, the area (the total surface area of the enclosure units 32) of each inner bag 3 can be minimized (to ⅓); therefore, as described above, it is possible to suppress scattering of the moisture to the outside of the accommodation unit 42. Further, in this case, similarly to the case above, by folding each inner bag 3 so that when the second sheet material 31 is air-impermeable, the second sheet material 31 is positioned as the uppermost surface in the vertical direction, and when the second sheet material 31 is air-permeable, an air-impermeable sheet material (not shown) that covers at least one of the first sheet material 31 and the second sheet material 32 is positioned as the uppermost surface in the vertical direction, it is possible to further effectively suppress easy scattering of the moisture.

Further, when four enclosure units 32 are provided in each inner bag 3, the inner bags 3 may be folded in various ways when they are accommodated in individual accommodation units 42 of the outer bag 4. However, the inner bags 3 are preferably accommodated in individual accommodation units 42 of the outer bag 4 while being folded twice or three times; that is, all of the enclosure units 32 are overlaid on one another, thereby minimizing the area (the total surface area of the enclosure units 32) of the inner bag 3 (to ¼). With this structure, as described above, it is possible to suppress scattering of the moisture in the accommodation unit 42 to the outside of the accommodation unit 42. Further, in this case, similar to the case above, by folding each inner bag 3 so that when the second sheet material 31 is air-impermeable, the second sheet material 31 is positioned as the uppermost surface in the vertical direction, and when the second sheet material 31 is air-permeable, an air-impermeable sheet material (not shown) that covers at least one of the first sheet material 31 and the second sheet material 32 is positioned as the uppermost surface in the vertical direction, it is possible to more effectively suppress easy scattering of the moisture in the enclosure units 32. When five or more enclosure units 32 are provided in each inner bag 3, similarly to the case above, the inner bags 3 are preferably accommodated in individual accommodation units 42 of the outer bag 4 while being folded several times at portions between adjacent enclosure units 32 so that one of the enclosure units 32 is disposed lowermost, and all other enclosure units 32 are laminated thereon.

Further, in order to suppress scattering of the moisture to the outside of the accommodation unit 42 as described above, the outer bag 4 of the disposable body warmer 1 of the present embodiment has two accommodation units 42 for accommodating the inner bag 3. The moisture in the exothermic composition 2 enclosed in the inner bag 3 is scattered from the front and rear surfaces (the wrapping films 40 and 41) of the accommodation unit 42, and may also be scattered from the side edges of the accommodation unit 42 in the four directions. However, when the outer bag 4 has two accommodation units 42, one of the side edges of each accommodation unit 42 is connected to another accommodation unit 42 via the second sealing portion 44. Therefore, even when the moisture in the exothermic composition 2 is scattered from one side edge of one of the accommodation units 42, the moisture will pass through the second sealing portion 44 and is scattered toward the other accommodation unit 42. As a result, the two accommodation units 42 exchange with each other the moisture scattered from the exothermic composition 2. Therefore, it is possible to accumulate the moisture from the exothermic composition 2 in the accommodation unit 42, thereby suppressing scattering of the moisture to the outside of the accommodation unit 42.

Further, to suppress the scattering of the moisture in the exothermic composition 2 from the accommodation unit 42, the first sealing portion 43 formed in the outer peripheral edge of the outer bag 4 preferably has high strength. If the first sealing portion 43 of the outer bag 4 has high strength, even when the moisture in the exothermic composition 2 is scattered from the three remaining side edges of the accommodation unit 42, the scattering of the moisture toward the outside can be blocked by the first sealing portion 43, thereby accumulating the moisture from the exothermic composition 2 in the accommodation unit 42. Although it depends on the width or conditions of the sealing, the strength of the first sealing portion 43 is preferably in a range of 10N/15 mm to 100N/15 mm. In contrast, the strength of the second sealing portion 44 between the two accommodation units 42 may be less than the strength of the first sealing portion 43, and is preferably in a range of 5N/15 mm to 80N/15 mm. The strengths of the first sealing portion 43 and the second sealing portion 44 may be measured by a test method according to JISZ 0238 1998. Further, the sealing width of the first sealing portion 43 is preferably 1 mm to 50 mm, more preferably 1 mm to 15 mm. Further, the sealing width of the second sealing portion 44 is preferably 1 mm to 50 mm, more preferably 1 mm to 15 mm. Further, the greater the length of the second sealing portion 44 relative to the length of the first sealing portion 43, more moisture in the exothermic composition 2 is scattered to the second sealing portion 44 than to the first sealing portion 43, thereby enabling, as described above, the adjacent accommodation units 42 to exchange the scattered moisture with each other, thus suppressing the scattering of the moisture in the exothermic composition 2 from the accommodation units 42. Similarly, when the second sealing portion 44 has a sealing width smaller than that of the first sealing portion 43, the moisture in the exothermic composition 2 will be more easily scattered from the second sealing portion 44 than from the first sealing portion 43, and is thus preferable.

As described above, the various factors above are important in ensuring a sufficient exothermic duration of the exothermic composition 2 by suppressing the scattering of the moisture in the exothermic composition 2 to the outside through the accommodation unit 42 of the outer bag 4. In addition, the present inventors found that, in particular, when the R value, which represents "the degree of difficulty in scattering of the moisture in the exothermic composition 2" and can be found by Formula (1) below, is 330 or greater, it is possible to desirably suppress the scattering of the moisture to the outside of the accommodation unit 42 of the outer bag 4, thereby further improving the prolonged exothermic duration of the exothermic composition 2.

$$R = A \times B \times \left\{ \frac{1}{2 \times C} - \frac{1}{D} + \frac{1}{E - F \times (G/H)} \right\} \geq 330 \qquad \text{Formula (1)}$$

The parameters A to H in Formula (1) above indicate the following.

A: Inclusion amount (g) of the exothermic composition 2 enclosed in the inner bag 3 in the accommodation unit 42

B: Moisture content (%) in the exothermic composition 2
C: Area (m²) of the accommodation unit 42
D: Number of enclosure units 32
E: Length (m) of outer peripheral sealing of the accommodation unit 42
F: Length (m) of inner peripheral sealing of the accommodation unit 42
G: Strength (N/15 mm) of outer peripheral sealing
H: Strength (N/15 mm) of inner peripheral sealing The area of the accommodation unit 42 represented by parameter C is an area in a plan view (one side). In this embodiment, as shown in FIG. 1, the area of the accommodation unit 42 means an area measured by subtracting the sealing portion 43 or 44 from the area (in a plan view) of each of the divisional regions 4A and 4B of the outer bag 4 when the outer bag 4 is divided into two portions at the sealing width center of the second sealing portion 44 by a divisional line D extending along the second sealing portion 44. In this embodiment (the example shown in FIG. 1), the area of the accommodation unit 42 is "x×y."

The inner peripheral sealing of the accommodation unit represented by parameter F is a region where adjacent accommodation units 42 enable exchange of scattered moisture via the second sealing portion 44, among the second sealing portion 44 disposed between adjacent accommodation units 42. The length of the inner peripheral sealing is defined as a length of an actual portion where the adjacent accommodation units 42 are opposed having the second sealing portion 44 between them, among length d (a distance from one end to the other end) of the second sealing portion 44. More specifically, as shown in FIG. 1, when the accommodation unit 42 has a rectangular shape, the length w of the straight line between the opposed adjacent accommodation units 42 corresponds to the length of the inner peripheral sealing. Further, as shown in FIG. 6, for example, when the accommodation unit 42 has a triangular shape, the length w of the straight line between the opposed adjacent accommodation units 42 corresponds to the length of the inner peripheral sealing. Further, as shown in FIG. 7, for example, when the accommodation unit 42 has a pentagonal shape, since the exchange of the scattered moisture between the adjacent accommodation units 42 via the second sealing portion 44 can be performed up to length d (a distance from one end to the other end) of the second sealing portion 44 beyond the straight line w between the opposed adjacent accommodation units 42, length d (a distance from one end to the other end) of the second sealing portion 44 corresponds to the length of the inner peripheral sealing. Further, as shown in FIG. 8, for example, when the accommodation unit 42 has a substantially D-letter shape, which is formed by linearly connecting each end of a circle partially having a cut-out portion (i.e., a C-letter shape), since the exchange of the scattered moisture between the adjacent accommodation units 42 via the second sealing portion 44 can be performed up to length d (a distance from one end to the other end) of the second sealing portion 44 beyond the straight line w between the opposed adjacent accommodation units 42, length d (a distance from one end to the other end) of the second sealing portion 44 corresponds to the length of the inner peripheral sealing. Further, as shown in FIG. 9, for example, when the accommodation unit 42 has a perfect circular shape, length d (a distance from one end to the other end) of the second sealing portion 44 corresponds to the length of the inner peripheral sealing.

The outer peripheral sealing of the accommodation unit 42 represented by parameter E is a region excluding the inner peripheral sealing from the first sealing portion 43 surrounding the accommodation unit 42, and a length of the outer peripheral sealing is defined as the length of a region excluding the portion overlapped with the inner peripheral sealing from the outer peripheral length (x+y+z+w) of the accommodation unit 42. More specifically, as shown in FIG. 1, when the accommodation unit 42 has a rectangular shape, the length of the outer peripheral sealing is the length of a region excluding the portion overlapped with the inner peripheral sealing from the outer peripheral length (x+y+z+w) of the accommodation unit 42, i.e., the length (x+y+z), which excludes the length (w) of the straight line between the opposed adjacent accommodation units 42, that is, the length of the inner peripheral sealing.

Further, as shown in FIG. 6, for example, when the accommodation unit 42 has a triangular shape, the length of the outer peripheral sealing corresponds to the length of a region excluding the portion overlapped with the inner peripheral sealing from the outer peripheral length (x+y+w) of the accommodation unit 42. More specifically, the length of the outer peripheral sealing corresponds to the length (x+y), which excludes the length (w) of the straight line between the opposed adjacent accommodation units 42, that is, the length of the inner peripheral sealing, from the outer peripheral length (x+y+w) of the accommodation unit 42.

Further, as shown in FIG. 7, for example, when the accommodation unit 42 has a pentagonal shape, the length of the outer peripheral sealing is a region excluding the portion overlapped with the inner peripheral sealing from the outer peripheral length (x+y+z+w+v) of the accommodation unit 42. More specifically, the length of the outer peripheral sealing is the length of a region (x'+y+z+v') resulting from cutting out length d of the second sealing portion 44 (i.e., a length of the outer peripheral sealing from point P1 to point P2, wherein P1 and P2 are intersection points of the accommodation unit 42, and each of the horizontal lines starting from the two ends of the second sealing portion 44 toward the accommodation unit 42); that is, resulting from cutting out the length of the inner peripheral sealing.

Further, as shown in FIG. 8, for example, when the accommodation unit 42 has a substantially D-letter shape, the length of the outer peripheral sealing corresponds to the length of a region excluding the portion overlapped with the inner peripheral sealing from the outer peripheral length (x+w) of the accommodation unit 42. More specifically, the length of the outer peripheral sealing corresponds to the length (x') of a region resulting from cutting out length d of the second sealing portion 44 (i.e., the outer peripheral length from point P1 to point P2, wherein P1 and P2 are intersection points of the accommodation unit 42 and each of the horizontal lines starting from the two ends of the second sealing portion 44 toward the accommodation unit 42), i.e., cutting out the length of the inner peripheral sealing. Further, as shown in FIG. 9, for example, when the accommodation unit 42 has a perfect circular shape, the length of the outer peripheral sealing also corresponds to the outer peripheral length (x') from P1 to P2.

Further, the strength of the outer peripheral sealing and the strength of the inner peripheral sealing represented by parameters G and H are measured by the strength measurement method explained above, and respectively correspond to the strength of the first sealing portion 43 and the strength of the second sealing portion 44.

In Formula (1) above, "A×B" represents an amount of moisture contained in the exothermic composition 2. The greater the moisture content, the longer the exothermic duration. Further, "2×C" represents the area (surface area) of the front and rear surfaces of the accommodation unit 42. As described above, when the surface area of the accommodation unit 42 for containing the inner bag 3 is small, it is possible to correspondingly suppress the scattering of the moisture in the exothermic composition 2 through the accommodation unit 42, thereby prolonging the exothermic duration. The area of one side of the accommodation unit 42 is preferably 0.0025 m$^2$ to 0.25 m$^2$, more preferably 0.01 m$^2$ to 0.05 m$^2$. Further, as described above, "−1/D" means that the area subjected to external contact of the exothermic composition 2 enclosed in each enclosure unit 32 of the inner bag 3 can be minimized (1/D) by containing the inner bag 3 in the accommodation unit 42 in a folded state, thereby suppressing the scattering of the moisture in the exothermic composition 2 enclosed in each enclosure unit 32, thus prolonging the exothermic duration. Further, "1/(E−F×(G/H))" means that, when the ratio of the length of the inner peripheral sealing to the length of the outer peripheral sealing in the accommodation unit 42 is large, more moisture in the exothermic composition 2 is scattered to the inner peripheral sealing (the second sealing portion 44) than to outer peripheral sealing (the first sealing portion 43) and the adjacent accommodation units 42 exchange the scattered moisture; thus, it is possible to suppress the scattering of the moisture in the exothermic composition 2 through the accommodation unit 42, thereby prolonging the exothermic duration. Further, "G/H" means that the strength of the inner peripheral sealing is smaller than the strength of the outer peripheral sealing, and the moisture in the exothermic composition 2 more easily passes through the inner peripheral sealing (the second sealing portion 44) than the outer peripheral sealing (the first sealing portion 43), and is scattered to the adjacent accommodation unit 42.

Table 1 shows the results of the measurement of R values mentioned above with respect to various types (Example 1 to 5 and Comparative Example 1) of disposable body warmer 1 of the present embodiment in which the outer bag 4 has two accommodation units 42, and the inner bag 3 having a plurality of enclosure units 32 is accommodated in each accommodation unit 42 in a folded state. Further, Table 1 also shows the results of the measurement of R values with respect to the disposable body warmers of Comparative Examples 2 to 14, including a disposable body warmer in which an inner bag having 1 or 4 enclosure units is accommodated in an outer bag having an accommodation unit, and a disposable body warmer in which an inner bag having an enclosure unit is accommodated in an outer bag having two accommodation units. Further, Table 1 further shows the results of measurement of the exothermic duration of the exothermic composition 2 for the body warmers of Examples 1 and 3 and Comparative Examples 1, 2, 6, and 8 when each disposable body warmer was stored unused for 3 or 6 months after the production under a severe test condition at a temperature of 40° C. and a humidity of 75%; and, thereafter, the body warmer was used by taking out the inner bag from the accommodation unit of the outer bag. FIG. 10 shows calculation results of exothermic duration decrease rates measured for individual examples based on the exothermic duration immediately after the production (initial stage). Storage of each disposable body warmer for 3 or 6 months under a severe test condition at a temperature of 40° C. and a humidity of 75% corresponds to storage of a disposable body warmer for 18 or 36 months under normal temperature.

TABLE 1

| | Number of Accommodation Units | Inclusion Amount of Exothermic Composition in Inner Bag (g) | Moisture Content Percentage (%) | Number of Enclosure Units | Area of Accomodation Unit (m2) | Length of Outer Peripheral Sealing (m) | Length of Inner Peripheral Sealing (m) | Width of Outer Peripheral Sealing (mm) | Width of Inner Peripheral Sealing (mm) | Strength of Outer Peripheral Sealing (N/15 mm) | Strength of Inner Peripheral Sealing (N/15 mm) | R Value |
|---|---|---|---|---|---|---|---|---|---|---|---|---|
| Example 1 | 2 | 20 | 0.3 | 2 | 0.01 | 0.285 | 0.12 | 5 | 10 | 42 | 42 | 333.4 |
| Example 2 | 2 | 45 | 0.3 | 2 | 0.018 | 0.428 | 0.12 | 5 | 10 | 42 | 42 | 412.1 |
| Example 3 | 2 | 30 | 0.3 | 2 | 0.01 | 0.285 | 0.12 | 5 | 10 | 42 | 42 | 500 |
| Example 4 | 2 | 30 | 0.3 | 4 | 0.01 | 0.285 | 0.12 | 5 | 10 | 42 | 42 | 502.3 |
| Example 5 | 2 | 45 | 0.3 | 2 | 0.01 | 0.285 | 0.12 | 5 | 10 | 42 | 42 | 750.1 |
| Comparative Example 1 | 2 | 15 | 0.3 | 2 | 0.01 | 0.285 | 0.12 | 5 | 10 | 42 | 42 | 250 |
| Comparative Example 2 | 2 | 10 | 0.3 | 1 | 0.01 | 0.285 | 0.12 | 5 | 10 | 42 | 42 | 165.2 |
| Comparative Example 3 | 2 | 15 | 0.3 | 1 | 0.01 | 0.285 | 0.12 | 5 | 10 | 42 | 42 | 247.8 |
| Comparative Example 4 | 1 | 20 | 0.3 | 1 | 0.02 | 0.57 | 0 | 5 | 0 | 42 | — | 154.5 |
| Comparative Example 5 | 1 | 30 | 0.3 | 1 | 0.02 | 0.57 | 0 | 5 | 0 | 42 | — | 231.8 |
| Comparative Example 6 | 1 | 40 | 0.3 | 1 | 0.02 | 0.57 | 0 | 5 | 0 | 42 | — | 309.1 |
| Comparative Example 7 | 1 | 20 | 0.3 | 4 | 0.02 | 0.57 | 0 | 5 | 0 | 42 | — | 159 |
| Comparative Example 8 | 1 | 30 | 0.3 | 4 | 0.02 | 0.57 | 0 | 5 | 0 | 42 | — | 238.5 |
| Comparative Example 9 | 2 | 30 | 0.3 | 1 | 0.01 | 0.285 | 0.12 | 5 | 10 | 42 | 42 | 495.5 |

TABLE 1-continued

| | Number of Accommodation Units | Inclusion Amount of Exothermic Composition in Inner Bag (g) | Moisture Content Percentage (%) | Number of Enclosure Units | Area of Accomodation Unit (m2) | Length of Outer Peripheral Sealing (m) | Length of Inner Peripheral Sealing (m) | Width of Outer Peripheral Sealing (mm) | Width of Inner Peripheral Sealing (mm) | Strength of Outer Peripheral Sealing (N/15 mm) | Strength of Inner Peripheral Sealing (N/15 mm) | R Value |
|---|---|---|---|---|---|---|---|---|---|---|---|---|
| Comparative Example 10 | 2 | 15 | 0.6 | 1 | 0.01 | 0.285 | 0.12 | 5 | 10 | 42 | 42 | 495.5 |
| Comparative Example 11 | 1 | 60 | 0.3 | 1 | 0.02 | 0.57 | 0 | 5 | 0 | 42 | — | 463.6 |
| Comparative Example 12 | 1 | 30 | 0.6 | 1 | 0.02 | 0.57 | 0 | 5 | 0 | 42 | — | 463.6 |
| Comparative Example 13 | 1 | 60 | 0.3 | 4 | 0.02 | 0.57 | 0 | 5 | 0 | 42 | — | 477.1 |
| Comparative Example 14 | 1 | 30 | 0.6 | 4 | 0.02 | 0.57 | 0 | 5 | 0 | 42 | — | 477.1 |

As shown in FIG. 10, the exothermic durations of the disposable body warmers (Examples 1 and 3) of the present embodiment did not significantly decrease, compared with those immediately after the production (initial stage), even though these body warmers were left in an unused state for a long period of time; that is, the exothermic durations were desirably retained. In contrast, for Comparative Examples 1, 2, 6, and 8, when body warmers were left in an unused state for a long period of time, the exothermic durations decreased, compared with those immediately after the production. After 36 months under normal temperature, the exothermic durations largely decreased, i.e., by about 15%. The R values of Comparative Examples 1, 2, 6, and 8 were all less than 330. FIG. 10 thus revealed that, in the disposable body warmer 1 of the present embodiment in which the R value is 330 or more, and the outer bag 4 has two accommodation units 42, each of which contains the inner bag 3 having a plurality of enclosure units 32 in a folded state, the exothermic duration of the exothermic composition 2 can be desirably retained even when the body warmer is kept in an unused state for a long period of time. As is clear from the results, the disposable body warmer 1 of the present embodiment makes it possible to prolong the exothermic duration. FIG. 10 shows only the measurement results of exothermic durations with respect to Examples 1 and 3 in which the R values are 333.4 and 500, respectively; however, since the R values of other examples, i.e., Examples 2, 4, and 5, were greater than 333.4 or 500, it is evident that the exothermic durations of the exothermic compositions in these examples can also be prolonged to the same extent as in Examples 1 and 3, or even longer.

Theoretically, the exothermic duration of the exothermic composition 2 can be prolonged by increasing the moisture content percentage in the exothermic composition. However, by simply increasing only the moisture content percentage, the viscosity of the exothermic composition significantly increases. In Comparative Examples 10, 12, and 14 in which the moisture content percentage was increased compared with Comparative Examples 3, 5, and 8, the viscosity of the exothermic composition significantly increased and the exothermic composition became sticky; consequently, the surface of the inner bag became sticky, and it was difficult to enclose the exothermic composition in the inner bag 3. This poses a drawback of failure of the production of a body warmer, as well as a drawback such that the temperature of the exothermic composition does not increase, and the body-warming function of the body warmer is lost. As is clear from the above, it is extremely difficult to produce a disposable body warmer capable of prolonging the exothermic duration simply by increasing the moisture content percentage in the exothermic composition. Further, it may be possible to increase the moisture content in the exothermic composition by increasing the total inclusion amount of the exothermic composition; however, by increasing the total inclusion amount of the exothermic composition, the amount of the exothermic composition to be enclosed in the enclosure unit of the inner bag becomes excessively large. In fact, in Comparative Examples 9, 11, and 13 in which the inclusion amount of the exothermic composition was increased compared with Comparative Examples 3, 5, and 8, by having a significantly excessive inclusion amount of the exothermic composition in the enclosure unit, the exothermic composition enters into the sealing portion upon sealing of the two sheet materials of the inner bag. This may result in failure of desirable sealing of the two sheet materials of the inner bag, thereby failing the formation of the inner bag 3. Therefore, it is extremely difficult to produce a disposable body warmer capable of prolonging the exothermic duration of the exothermic composition 2 simply by increasing the total inclusion amount of the exothermic composition.

A method for using the disposable body warmer 1 having the above structure is described below. First, the inner bag 3 is retrieved by opening one of the accommodation units 42 of the outer bag 4. Here, it is possible to provide a simple opening means, such as a notch, in each of the accommodation units 42 of the outer bag 4. Then, a release paper for covering the adhesive layer, or an air-impermeable sheet material for covering at least one of the surfaces of the first sheet material 31 and the second sheet material 32 is removed from the inner bag 3, and the body warmer is disposed so that the exothermic composition 2 is attached to a desired body part. By thus disposing the disposable body warmer 1, the part where the body warmer is attached can be warmed by the heat generated from the exothermic composition 2.

In the disposable body warmer 1 having the above structure, the outer bag 4 has two accommodation units 42, and the inner bag 3 having a plurality of enclosure units 32 is accommodated in each accommodation unit 42 in a folded state. With this structure, as described above, ingenuity is exercised to the shapes of the inner bag 3 and outer bag 4 so that the inner bag 3 can be accommodated in the outer bag 4 with as little scattering of the moisture in the exothermic composition 2 enclosed in the inner bag 3 from the accommodation unit 42 as possible. Therefore, if the disposable body warmer is left unused for a long period of time, for example, because the disposable body warmer is kept in a store for a long time, it is possible to suppress a decrease in exothermic duration due to a decrease in moisture content percentage of the exothermic composition 2, thereby retaining the original exothermic duration estimated at the time of the production for a long period of time. Therefore, even when the disposable body warmer 1 is used after it was left unused for a long time, the desired exothermic duration estimated at the time of the production can be ensured. Further, since parameters A to H of the exothermic composition 2, the inner bag 3, and the outer bag 4 are set so that the R value found by Formula (1) above becomes 330 or greater, it is possible to further desirably prolong the original exothermic duration estimated at the time of the production of the disposable body warmer. The exothermic duration estimated at the time of the production is usually advertised, for example, in the form of an indication on the surface of the outer bag 4. This ensures that the user who actually uses the body warmer is not misled. Further, it becomes possible to prevent, for example, a case where the user has to discard an unused disposable body warmer because the estimated exothermic duration at the time of the production was not obtained. Further, unlike conventional body warmers that have prolonged exothermic durations by increasing the inclusion amount of the exothermic composition, it is not necessary to needlessly increase the inclusion amount of the exothermic composition. This eliminates the need for extra cost, and enables more convenient portability or use of the disposable body warmer 1.

Further, by containing the inner bag 3 in the outer bag 4 in a folded state, i.e., in a compact state, the required amount of the outer bag 4 (wrapping films 40 and 41) may be reduced compared with the case of containing the inner bag 3 in an unfolded state, thereby reducing material cost.

Further, by folding the inner bag 3 so that the air-impermeable sheet material is positioned as the uppermost surface in the vertical direction, it is possible to prevent easy scattering of the moisture in the exothermic composition 2 enclosed in each enclosure unit 32 of the inner bag 3, thereby further desirably retaining the exothermic duration at the time of the production for a long period of time.

An embodiment of the present invention has been explained above; however, the present invention is not limited to the embodiment above, and various modifications are possible within a scope in which the gist of the present invention is retained. For example, in the above embodiment, the enclosure unit 32 of the inner bag 3 has a rectangular shape; however, the shape of the enclosure unit 32 is not limited to a rectangle, but may be other various shapes including polygonal shapes such as triangle or pentagon, circular shapes, and elliptical shapes. The inner bag 3 may also have various shapes corresponding to the various shapes of the enclosure unit 32. Further, the shape of the accommodation unit 42 of the outer bag 4 is also not limited to a rectangle, a triangle, a pentagon, a circle, or a substantially D-letter shape, but may be other various shapes including other polygonal shapes and elliptical shapes. The outer bag 4 may also have various shapes corresponding to the various shapes of the accommodation unit 42.

Further, in the above embodiment, the inner bag 3 has at least two partitioned enclosure units 32, and is accommodated in the accommodation unit 42 in a folded state so that one of the enclosure units 32 is overlaid on another enclosure unit 32; however, as shown in FIGS. 13 and 14, it is also possible that the inner bag 3 having only one enclosure unit 32 is accommodated in each accommodation unit 42 of the outer bag 4. In this case, as shown in FIGS. 11 and 12, a plurality of (2 in the figures) inner bags 3 are accommodated in each accommodation unit 42 while being stacked on each other so that an enclosure unit 32 of one inner bag 3 is overlaid on an enclosure unit 32 of at least one of the other inner bags 3. With this structure, the same advantageous effects as those of the above embodiment can be obtained; it is possible to suppress scattering of the moisture in the exothermic composition 2 from the outer bag 4; and the exothermic duration of the exothermic composition 2 can be desirably retained, even when the disposable body warmer is kept in an unused state for a long period of time. This embodiment is also preferably structured such that the inner bags 3 are stacked on each other so that the air-impermeable sheet material is positioned as the uppermost surface in the vertical direction. Since this structure prevents easy scattering of the moisture in the exothermic composition 2 enclosed in the enclosure unit 32 in each inner bag 3, it is possible to further retain the exothermic duration at the time of production for a long period of time. The fundamental structure of the embodiment shown in FIGS. 11 and 12 is similar to the structure of the embodiment shown in FIGS. 1 and 2. Therefore, the reference numbers used in FIGS. 1 and 2 are also used in FIGS. 11 and 12, and a detailed explanation is omitted.

Further, as shown in FIG. 16, a so-called non-stick-type body warmer (inner bag 3) having only one enclosure unit 32 may also be structured such that, as shown in FIG. 15, a plurality of (2 in the figures) inner bags 3 are accommodated in each accommodation unit 42 of the outer bag 4 while being stacked on each other so that an enclosure unit 32 of one inner bag 3 is overlaid on an enclosure unit 32 of at least one of the other inner bags 3. With this structure, the same advantageous effects as those of the above embodiment can be obtained; it is possible to suppress scattering of the moisture in the exothermic composition 2 from the outer bag 4; and the exothermic duration of the exothermic composition 2 can be desirably retained, even when the disposable body warmer is kept in an unused state for a long period of time. The fundamental structure of the embodiment shown in FIG. 16 is similar to the structure of the embodiment shown in FIGS. 1 and 2. Therefore, the reference numbers used in FIGS. 1 and 2 are also used in FIG. 16, and a detailed explanation thereof is omitted.

DESCRIPTION OF REFERENCE NUMERALS

1: Disposable Body Warmer
2: Exothermic Composition
3: Inner Bag
4: Outer Bag
32: Enclosure Unit
40 and 41: Wrapping Films 42: Accommodation Unit
43: First Sealing Portion
44: Second Sealing Portion

The invention claimed is:

1. A disposable body warmer in which an exothermic composition that contains moisture and generates heat by contact with air is enclosed in one or more air-permeable inner bags, which are accommodated in an airtight outer bag,
the outer bag comprising two accommodation units that are partitioned from each other and capable of containing the one or more inner bags,
the one or more inner bags each comprising at least one enclosure unit capable of enclosing the exothermic composition, and are accommodated in each accommodation unit in a manner such that at least one of the enclosure units is overlaid with another enclosure unit,
the outer bag being formed by overlaying two wrapping films with each other, sealing an entire outer peripheral edge, and partitioning the two accommodation units by sealing, and
Parameters A to H being set to satisfy Formula (1) below, $$R = A \times B \times \left\{ \frac{1}{2 \times C} - \frac{1}{D} + \frac{1}{E - F \times (G/H)} \right\} \geq 330 \quad \text{Formula (1)}$$

wherein A represents the inclusion amount (g) of the exothermic composition enclosed in each inner bag in each accommodation unit; B represents the moisture content percentage (%) in the exothermic composition; C represents the area (m²) of the accommodation unit; D represents the number of the enclosure units; E represents the length (m) of an outer peripheral sealing of the accommodation unit; F represents the length (m) of an inner peripheral sealing of the accommodation unit; G represents the strength (N/15 mm) of the outer peripheral sealing; and H represents the strength (N/15 mm) of the inner peripheral sealing.

2. The disposable body warmer according to claim 1, wherein each inner bag comprises at least two enclosure units partitioned from each other, and is accommodated in the accommodation unit in a single-folded state so that at least one of the enclosure units is overlaid with another enclosure unit.

3. The disposable body warmer according to claim 2, wherein the number of the enclosure units is 2 to 4.

4. The disposable body warmer according to claim 3, wherein one of the enclosure units is disposed lowermost, and all other enclosure units are stacked thereon.

5. The disposable body warmer according to claim 4, wherein an air-impermeable sheet material is stacked on at least one surface of the inner bag, and the enclosure units are stacked in a manner such that the air-impermeable sheet material is positioned as the uppermost surface in the vertical direction.

6. The disposable body warmer according to claim 2, wherein one of the enclosure units is disposed lowermost, and all other enclosure units are stacked thereon.

7. The disposable body warmer according to claim 6, wherein an air-impermeable sheet material is stacked on at least one surface of the inner bag, and the enclosure units are stacked in a manner such that the air-impermeable sheet material is positioned as the uppermost surface in the vertical direction.

8. The disposable body warmer according to claim 1, wherein each inner bag comprises one enclosure unit, and a plurality of the inner bags are accommodated in each accommodation unit while being stacked on each other so that an enclosure unit of one of the inner bags is overlaid with an enclosure unit of at least one of the other inner bags.

9. The disposable body warmer according to claim 8, wherein one of the enclosure units is disposed lowermost, and all other enclosure units are stacked thereon.

10. The disposable body warmer according to claim 9, wherein an air-impermeable sheet material is stacked on at least one surface of the inner bag, and the enclosure units are stacked in a manner such that the air-impermeable sheet material is positioned as the uppermost surface in the vertical direction.

* * * * *